United States Patent [19]

Kupperman et al.

[11] Patent Number: 4,959,548
[45] Date of Patent: Sep. 25, 1990

[54] NEUTRON APPARATUS FOR MEASURING STRAIN IN COMPOSITES

[75] Inventors: David S. Kupperman, Oak Park; Saurindranath Majumdar, Naperville; John F. Faber, Jr., Downers Grove; J. P. Singh, Bolingbrook, all of Ill.

[73] Assignee: The United States of America as represented by the United States Department of Energy, Washington, D.C.

[21] Appl. No.: 346,762

[22] Filed: May 2, 1989

[51] Int. Cl.$^5$ .......................................... G01N 23/207
[52] U.S. Cl. ..................... 250/390.09; 250/390.01; 250/390.07; 250/390.08; 378/72
[58] Field of Search ............... 250/390.09, 390.08, 250/390.07, 390.01, 391, 392; 378/75, 72

[56] References Cited

U.S. PATENT DOCUMENTS 3,934,138  1/1976  Bens ...................................... 378/72

FOREIGN PATENT DOCUMENTS 1293594  2/1987  U.S.S.R. ............................ 250/390.09

OTHER PUBLICATIONS

A. D. Krawitz, R. Roberts and J. Faber, "Residual stress relaxation in cemented carbide composites," Inst. Phys. Conf., Ser. No. 75: Chapter 6 (1966) pp. 577–589; ©1986 Adam Hilger Ltd.

A. J. Allen, M. t. Hutchings, C. G. Windsor and C. Andreani, "Neutron diffraction methods for the study of residual stress fields," Advances in Physics, vol. 34, No. 4 (1985) pp. 445–473; ©1985 Ukaea, Harwell.

S. R. MacEwen, J. Faber, Jr. and A. P. L. Turner, "The of Time–of–Flight Neutron Diffraction to Study Grain Interaction Stresses," Acta Metall., vol. 31, No. 5 (1983) pp. 657–676; Pergamon Press Ltd.

Primary Examiner—Constantine Hannaher
Attorney, Agent, or Firm—Helen S. Cordell; John M. Albrecht; William R. Moser

[57] ABSTRACT

A method and apparatus for orienting a pulsed neutron source and a multi-angle diffractometer toward a sample of a ceramic-matrix or metal-matrix composite so that the measurement of internal strain (from which stress is calculated) is reduced to uncomplicated time-of-flight measurements.

12 Claims, 6 Drawing Sheets

NEUTRON APPARATUS FOR MEASURING STRAIN IN COMPOSITES

CONTRACTUAL ORIGIN OF THE INVENTION

The United States Government has rights in this invention pursuant to Contract No. W-31-109-ENG-38 between the U.S. Department of Energy and the University of Chicago.

BACKGROUND OF THE INVENTION

This invention relates to a method and apparatus for measuring nondestructively, in situ, and in real time, the internal strains from which stresses in composites can be determined. Utilizing an intense pulsed neutron source, a general purpose multi-angle diffractometer and uncomplicated time-of-flight measurements, the invention enables characterization of interfacial bonds in fibers and matrix of metal-matrix and ceramic-matrix composites.

Advanced fiber-reinforced composite materials consisting of a matrix (ceramic or metal, herein called a matrix) and an inclusion (fiber, whisker or particle, herein called a fiber) are being developed for applications in defense, aerospace, energy conservation, and transportation industries. The strength and toughness of fiber-reinforced composites are controlled to a large extent by the nature of bonding between the fibers and the matrix. Ceramic-ceramic composites generally require weak interfacial bonding to achieve high toughness. In certain systems, chemical bonding is supposed to be nonexistent, and frictional forces at the interfaces provide the necessary link between the fibers and the matrix. These frictional forces are dependent on the residual stresses that develop during cooldown after sintering, and it is important to have an idea of the residual stresses that exist in such composites, particularly at the fiber-matrix interface, and of the redistribution of stresses between fiber and matrix due to slippage, cracking or plastic yielding.

It is well known in the prior art that x-ray and neutron diffraction can be used for measuring strain in crystalline metallic or ceramic composites. Change in the interplanar spacing of a set of crystal lattice planes due to strain causes a change in the diffraction angle of the scattered x-ray or neutron beam, and from this change the magnitude of the strain can be determined. Prior art methods using x-ray diffraction are limited, however, because they rely on the relatively weak penetrability of x-rays. X-rays can only measure changes in interplanar spacing at or near the surface of the composite, where the strain that is measured is subject to surface distortion; in most cases x-rays cannot penetrate deep enough to measure bulk strain and thus provide a measure of bulk internal stress at the fiber-matrix interface.

It is also known in the prior art that neutrons can penetrate deeper than x-rays and thus neutron diffraction techniques can provide a bulk or internal measurement. Thermal neutrons are of interest for stress measurements in that they have wavelengths on the order of the lattice spacing, allowing application of Bragg's Law of diffraction to neutrons as:

$$2d_{hkl} \sin \theta = \lambda_{hkl} \quad (1)$$

Where d is the lattice spacing, $2\theta$ is the angle between incident and scattered neutron beams when a Bragg peak is detected, $\lambda$ is the deBroglie wavelength of the neutron, and h, k, and l are the Miller indices of the diffracting plane.

As is also well known in the prior art, the determination of stress requires the measurement of strain in at least two spatial directions, and measurement of stress in real-time, for example during applied load or thermal cycling, requires that those two measurements are made simultaneously. With a reactor as a source, a monochromatic neutron beam is used to look in only one spatial direction so that prior art neutron diffraction methods cannot provide the simultaneous measurements of strain in two spatial directions which are necessary for the realtime measurement of stress.

The use of a reactor source in combination with a single angle diffractometer is also very cumbersome and potentially slow because the diffractometer—a bulky, sensitive instrument—must be moved through multiple angles to find the angle at which a Bragg peak is obtained.

In the prior art, a pulsed neutron source which provides a polychromatic beam has been used in combination with a multi-angle diffractometer to detect diffracted beams at multiple angles. However, prior to this invention practitioners have failed to recognize the application to fiber reinforced composites, in that the two instruments in combination enable the simultaneous measurement of strain in the required two directions and the resultant calculation of residual stress.

The present invention uses the General Purpose Powder Diffractometer (GPPD) at the Intense Pulsed Neutron Source (IPNS) at Argonne National Laboratory but is not limited to that equipment. The IPNS produces neutrons by spallation, by bombarding a uranium target with 450 MeV protons. The pulse repetition rate is 30 cycles/s with a peak thermal flux of about $4 \times 10^{14}$ neutrons/cm$^2$. For neutron scattering studies, the fast neutrons are moderated by hydrogenous moderator materials to provide white-beam (polychromatic) slow neutrons.

The GPPD is about 20m from the target. Neutrons are detected with banks of $^3$He proportional counters (140 total) encircling the sample chamber on a 1.5m scattered flight path, at 20°, 30°, ±60°, ±90°, and ±148° relative to the neutron forward direction. Data are collected by a PDP 11/34-Z8000 computer. With the detectors fixed, the GPPD uses time-of-flight techniques, well known in the prior art, to determine the various wavelength components in a particular scattering experiment.

Prior to the present invention researchers using the IPNS and the GPPD at Argonne National Laboratory have simply applied prior art techniques developed with other equipment configurations and have thus failed to realize the full potential for composites of the powerful combination of the GPPD and IPNS. Until this invention researchers using neutron diffraction to measure stress in an ordered composite have failed to realize that positioning of two detectors as taught in this invention allows the simultaneous measurement of strain in two spatial directions thus reducing the determination of residual stress in the fiber and matrix to acceptable levels of effort.

It is an object of this invention to provide an improved method for the measurement of strain in metal-matrix and ceramic-matrix composites.

It is another object of this invention to provide an improved method for the determination of stress in a stressed sample of an ordered ceramic or metal-matrix composite.

It is another object of this invention to provide a method and apparatus for the measurement of strain which is nondestructive, and effective in air, vacuum or a gaseous environment.

It is another object of this invention to provide a method and apparatus for the measurement of spatial variations of strain within a ceramic or metal-matrix composite.

It is another object of this invention to provide an improved method and apparatus for the measurement of internal strain between a fiber and the matrix in which it is included, enabling nondestructive, in situ, and real time determination of residual stress in a ceramic or metal-matrix composite.

It is another object of this invention to provide an improved method and apparatus for the validation and calibration of other techniques for the measurement of strain and determination of stress (e.g. ultrasonic techniques) and the validation of models used to predict the mechanical behavior of advanced structural composites.

Additional objects, advantages and novel features of the invention will become apparent to those skilled in the art upon examination of the following and by practice of the invention.

SUMMARY OF THE INVENTION

To achieve the foregoing and other objects, this invention comprises a method and apparatus for orienting a pulsed neutron source and a multi-angle diffractometer toward a sample of an ceramic or metal-matrix composite so that the measurement of internal strain (from which stress is calculated) is reduced to uncomplicated time-of-flight measurements. A sample of a ceramic-matrix or metal-matrix composite is oriented so that the polychromatic beam from a pulsed neutron source is incident upon the sample at an angle of 45° to the longitudinal direction of the fibers embedded in the matrix which are to be examined. A multiangle diffractometer is oriented so that two detectors equidistant from the sample are at angles of 90° and 270° to the incident beam. At each of these angles, the wavelength within the polychromatic beam which is diffracted at maximum intensity (the Bragg peak) is isolated and the deBroglie wavelength of the diffracted neutron beams are calculated for a particular set of lattice planes.

Given the wavelengths of two scattered neutron beams, Bragg's law will then provide two measures of the lattice spacing of the composite. If the interplanar spacing of a sample is measured at the requisite constant angles in a strain free sample, and then measured in the strained composite, the magnitude of the change in interplanar spacing of the ceramic or metal-matrix composite will yield a measure of the residual strain, which can then be used to calculate the magnitude of the residual stress. Because the current invention uses fixed angles of incidence and reflection, calculation of the stress between the fiber and the matrix is reduced to a comparison of the time-of-flight of neutrons diffracted from a strain free sample versus the strained composite.

BRIEF DESCRIPTION OF THE DRAWINGS

The present invention is illustrated in the accompanying drawings where.

DETAILED DESCRIPTION OF THE INVENTION

Figure 1:
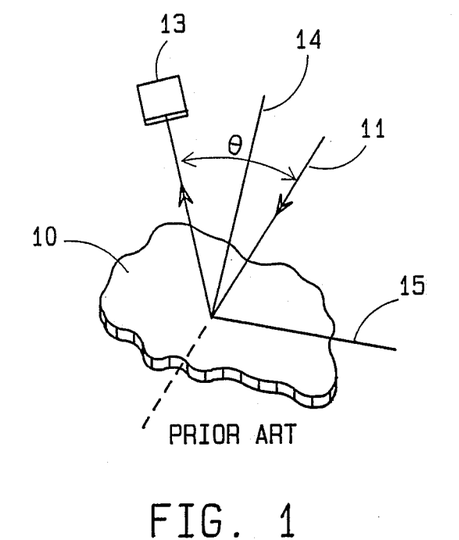
FIG. 1 is a schematic depicting the prior art, showing a monochromatic neutron beam directed toward a random crystalline composite, enabling the use of Bragg's law to measure the interplanar spacing of the crystal lattice planes.

As shown in FIG. 1, depicting the prior art, a monochromatic x-ray or neutron beam 11 of known wavelength $\lambda$ is incident upon the surface of a sample 10 of a random oriented crystal. The incident beam 11 is diffracted at maximum intensity at an angle $\theta$ which the incident beam 11 makes with the lattice plane 15, when, following Bragg's law, $$\sin \theta = \lambda/2d \qquad (2)$$

where d (not shown) is the interplanar spacing of the crystalline lattice planes of the sample 10. The diffracted ray 12 is received by the detector 13 which may be oriented to receive the diffracted ray 12 by rotating the detector 13 about the center of the irradiated specimen area, or, by rotating the sample 10.

Strain in the direction 14 normal to the lattice plane 15 will cause a change of the interplanar spacing d (not shown) and a consequent change in the diffraction angle $\theta$. A second measurement may be obtained by again rotating the detector 13 and placing a second detector to receive the second diffracted ray (not shown). The magnitude of the strain 14 can be determined from the change in the scattering angle $2\theta$.

For a randomly oriented sample there must be sufficient number of crystallites present in the sample with planes perpendicular to the direction in which the strain is to be measured for the diffraction peak to be observed. Also, the lattice spacing of the unstrained material must be known if the absolute strain is required.

Figure 2:
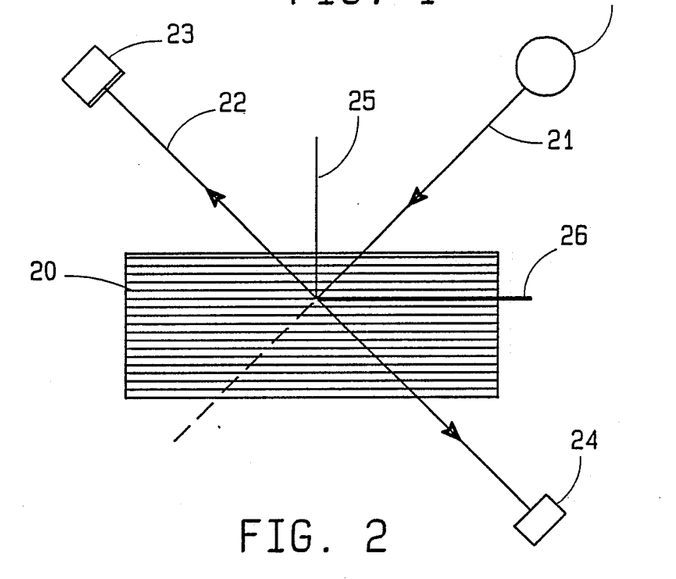
FIG. 2 is a schematic depicting the current invention, showing a polychromatic beam directed toward an ordered crystalline composite at the angles prescribed by the current invention.

FIG. 2 is a schematic depicting the current invention. Referring to FIG. 2, a sample of a fiber reinforced ceramic or metal-matrix composite is oriented so that a polychromatic neutron beam 21 from a pulsed source 27 is incident upon the parallel lattice planes 20 of the fibers embedded in the matrix and oriented at an angle of 45° to the longitudinal direction of the lattice planes 20. A detector 23 isolates the Bragg diffraction peak. Because the scattering angle is fixed, time-of-flight techniques known in the prior art can be used to determine the diffracted wavelength of maximum intensity by rewriting Bragg's law in terms of t, the time taken for a neutron to travel the total flight path L, $$\lambda = ht/mL = 2d \sin\theta \quad (3)$$

where d is the interplanar spacing, $\lambda$ is the neutron wavelength, h is Planck's constant, and m is the mass of the neutron.

The current invention departs from the methods of the prior art by adding a second detector 24 opposite detector 23, normal to the incident beam 21 and at the same distance from the incident beam 21 as detector 23. Strain 25 and strain 26 are then measured along the bisector of the angles between the path of the incident beam 21 and the line between the detector 23 and the detector 24.

Applying the method of the current invention to the calculation of the residual stress in a fiber-matrix composite, Bragg's law (Equation 1 above) is used first to determine the lattice spacing d for particular hkl reflections from both matrix and fiber averaged over a volume of the powdered and thus strain-free matrix and fiber. The stressed composite is examined next. The lattice strain associated with the hkl plane of a given phase in the composite is given by $$e = (d - d_0)/d_0 \quad (4)$$

where $d_0$ is the unstrained hkl spacing and d is the spacing for the composite. Because the scattering angle is fixed at $2\theta$, applying the time-of-flight-techniques described above, $$e = \Delta\lambda/\lambda = \lambda t/t \quad (5)$$

allows the residual strain to be measured and residual stress to be calculated using methods known in the prior art.

The method and apparatus of the current invention was applied to an alumina ($Al_2O_3$)/SiC ceramic-matrix composite. The lattice spacings d for particular hkl reflections from both $Al_2O_3$ and SiC were averaged over a volume of the strain-free powder. Next, the stressed composite was examined. The lattice strain associated with the hkl spacing in the composite is given by $$e = (d - d_0)/d_0 \quad (4)$$

For SiC, the diffraction peaks of principal interest are the {111} and {220} since the [111]and [$\bar{2}0$]crystallographic directions are parallel and perpendicular to the SiC fiber axes, respectively. In principle, the stresses in the fiber could be calculated from the residual strains in these directions. The ceramic-matrix samples used in this study were SiC fibers (15% and 25% by weight) reinforced $Al_2O_3$ matrix composites hot-pressed into samples $30 \times 25 \times 5$ mm thick. The fibers are $\sim 10$–$30$ $\mu m$ long and $\sim 0.75$ $\mu m$ in diameter. The fibers have a high defect density, primarily due to stacking faults. Although the predominant neutron diffraction peaks for these samples were those associated with the $\beta$ (cubic) form, the presence of a $\alpha$ (hexagonal) form cannot be ruled out completely. In order to carry out the strain and stress analysis, the cubic structure is assumed. This assumption should not result in serious analytical errors as the {111} and {220} planes of the cubic structure have the same lattice spacing as the {0006} and {11$\bar{2}$0} planes of the hexagonal structure, and the [111] direction of the cubic structure and [0006] of the hexagonal structure are both parallel to the fiber axis.

Figure 3:
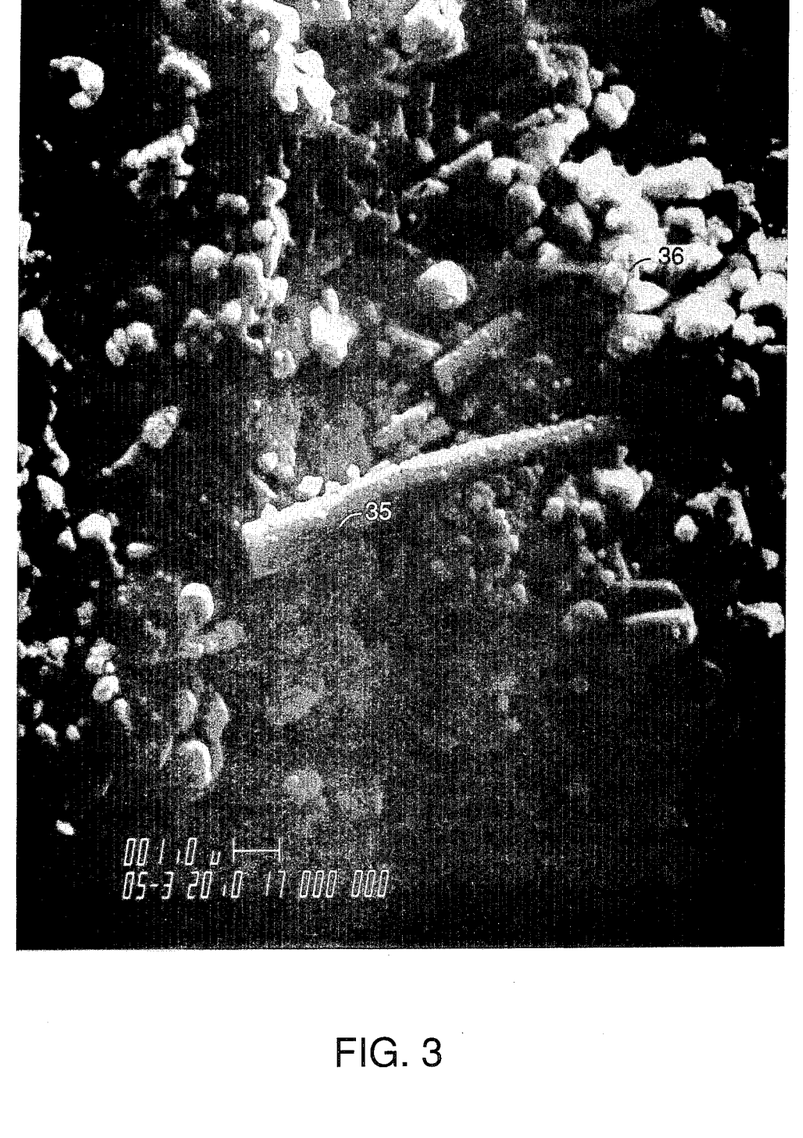
FIG. 3 is a micrograph of a ceramic-matrix composite, an $Al_2O_3/SiC$ sample, showing SiC whiskers and $Al_2O_3$ grains.

Although the fibers are randomly distributed in the powder before pressing, the hot-pressing process results in some texturing because few fibers are oriented with the long axis parallel to the pressing direction. In FIG. 3, a micrograph of a fracture surface of this sample shows the SiC fibers 35 and $Al_2O_3$ grains 36 and clearly indicates fiber pull-out, suggesting a less than perfect fiber-matrix bond. The pressing direction is from top to bottom.

Figure 4A:
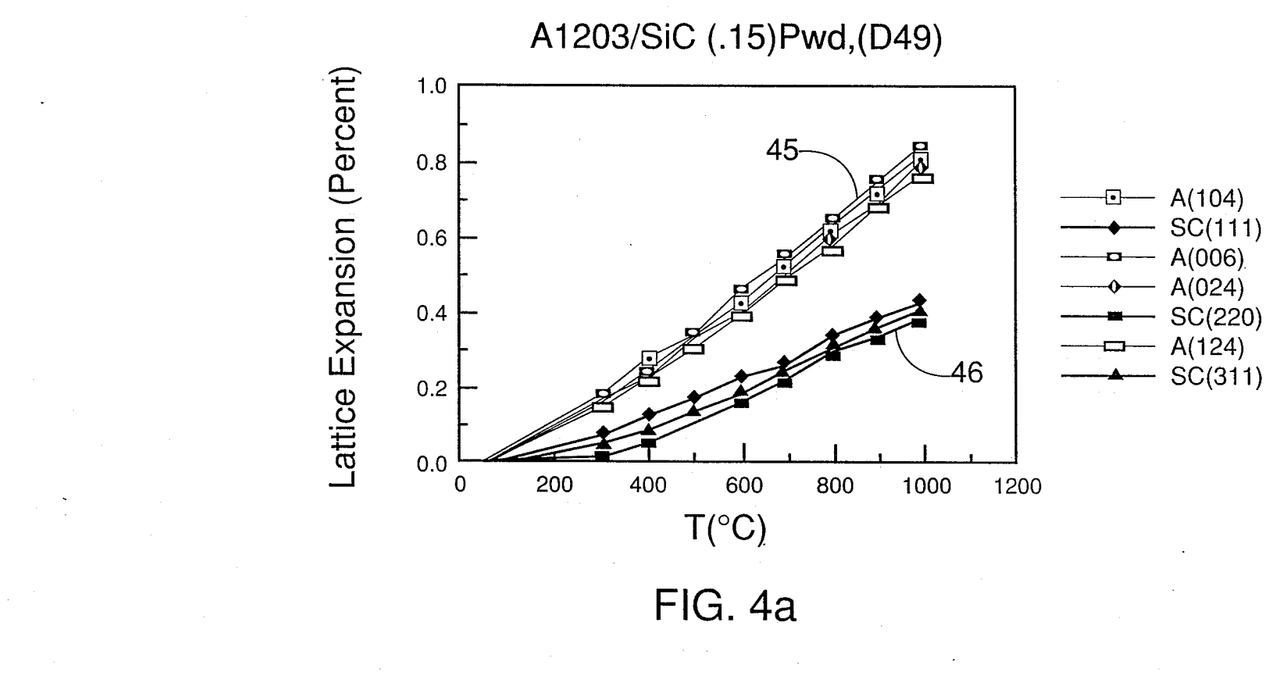
FIGS. 4a and 4b are graphs depicting the lattice expansion of various $Al_2O_3$ and SiC planes for both powder (FIG. 4a) and hot-pressed samples (FIG. 4b).
Figure 4B:
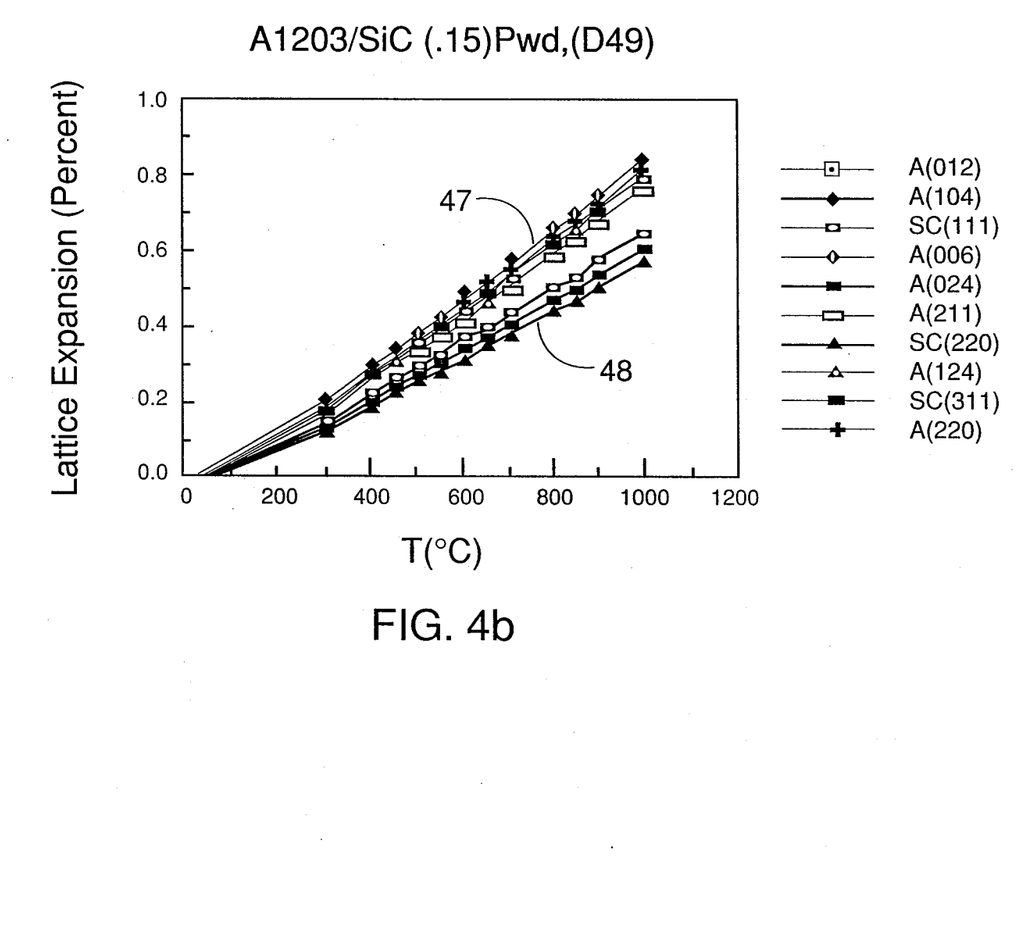

Cooling the hot-pressed composite after forming could cause high residual compressive stresses in the fibers due to differential thermal contraction. From 0° C. to 1000° C., the thermal expansion of $Al_2O_3$ is $8.8 \times 10^{-6}$° $C.^{-1}$. Lattice expansion and residual strains were measured at temperatures from 25° C. to 1000° C. in a specially designed furnace. The sample was encapsulated in a vanadium tube and held at each temperature for two hours to acquire enough neutron counts. FIG. 4a shows the expansion of the lattice spacing versus temperature for various $Al_2O_3$ planes 45 and SiC planes 46 in the powder. Similarly, FIG. 4b shows the expansion of the lattice spacing versus temperature for various $Al_2O_3$ planes 47 and SiC planes 48 in the hot-compressed composite with 15% fiber content. A comparison of the results obtained from the powder with those obtained from the composite indicates that, in the hot-pressed sample, the strains (and thus stresses) in the SiC fibers, on the average, are substantially higher than the strains of the $Al_2O_3$. This is the result of the higher stiffness and lower volume fraction of the SiC. As the temperature is raised (relaxing the thermally induced stresses), the SiC lattice spacing increases much faster in the composite than in the powder, showing that the fibers were under substantial compressive stress. The magnitude of the difference for the matrix is much smaller, indicating much less stress on the average in the matrix. Table 1 shows representative values of mean thermal expansion coefficients for several crystallographic directions in the temperature range 25–1000° C., calculated from the data of FIG. 4. These results are close to those known in the prior art (see further Kingery et al., *Introduction to Ceramics*, Wiley and Sons, New York, 1975, p. 595).

TABLE 1

| Mean Thermal Expansion Coefficients of $Al_2O_3$ and SiC at 25–1000° C. ($\mu m/(\mu m/°C.) \times 10^{-6}$) | | | |
|---|---|---|---|
| $Al_2O_3$ | | SiC | |
| (hkl) | ($\alpha$) | (hkl) | ($\alpha$) |
| (104) | 8.5 | (111) | 4.5 |
| (006) | 8.6 | (220) | 4.2 |
| (024) | 9.1 | (311) | 4.3 |
| (221) | 7.8 | (422) | 5.5 |
| Average | 8.3 | | 4.6 |

Figure 5:
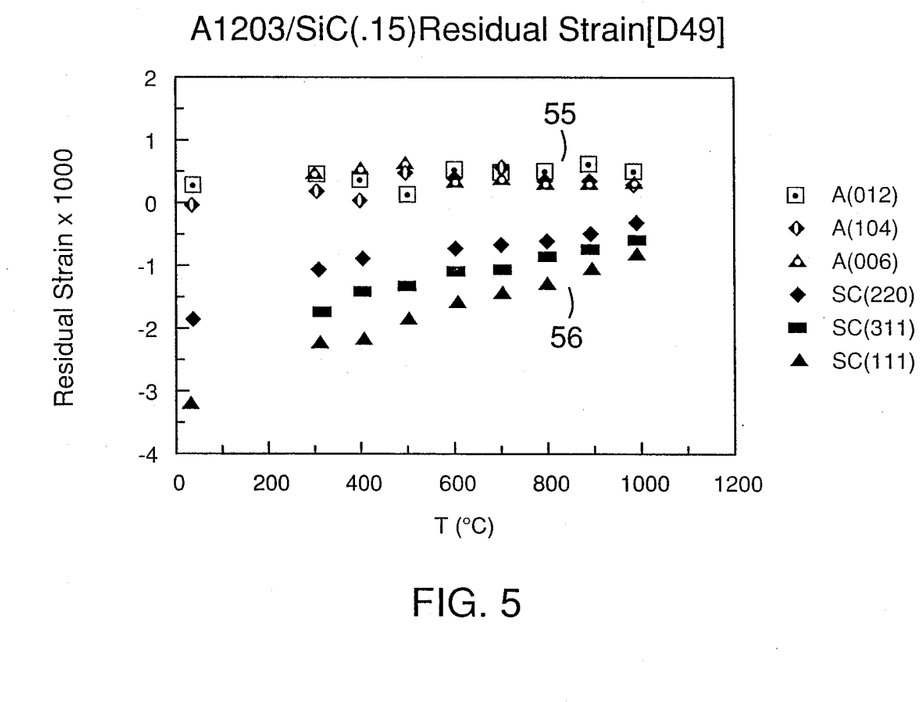
FIG. 5 is a graph depicting the residual strain versus the temperature for various planes of $Al_2O_3/SiC$.

FIG. 5 shows residual strains obtained from the differences in lattice spacing data between hot-pressed and powder samples for various crystallographic directions in $Al_2O_3$ planes 55 and SiC planes 56. Again it is clear that the magnitude of the strains, and thus the stresses, in the SiC fibers is much larger than in the $Al_2O_3$ matrix. Furthermore, the strains asymptotically approach 0 as the strains are relieved by thermal expansion. The strain appears to be totally relieved at 1300–1400° C. This is consistent with the idea that, on cooling from hot pressing, strain starts to build up significantly a few hundred degrees below the fabrication temperature of about 1700° C. That is, above 1400° C., the stresses are relieved.

The magnitude of the residual strain depends on the magnitude of the difference between thermal expansion coefficients of the effective matrix and the fiber.

$$e \sim (\bar{\alpha} - \alpha_f) \quad (6)$$

where $\alpha$ is the coefficient of thermal expansion of the effective matrix and $\alpha_f$ is that of the fiber. If the concentration of fibers increases, bringing the effective thermal expansion coefficient of the composite as seen by a single fiber closer to the fiber value, the strain should be reduced accordingly.

Analytical estimates of the residual strains in $Al_2O_3$ SiC were determined by using two self-consistent models: (1) a plane strain composite cylinder model and (2) Eshelby's ellipsoidal inclusion theory. The model assumes (a) a random collection of fibers, (b) plane strain, (c) the fiber is transversely isotropic while the matrix is isotropic, (d) the bond between fiber and matrix is perfect, (e) the interaction between fibers is negligible, and (f) there is a characteristic temperature below which the rates of stress relaxation are too slow to have an effect on stress. The two models gave almost identical estimates of the strains in the whiskers. Details of these model calculations are presented in Majumdar et al., "Determination of Residual Thermal Stresses in a SiC-/Al$_2$O$_3$ Composite Using Neutron Diffraction", *J. Am. Ceram. Soc.*, Volume 71:Number 10, pp. 858-863 (1988) which is incorporated herein by reference.

Comparison between the computed and the measured strains for the matrix composite by the method of the current invention was not as straightforward as it may first appear because the measured strains do not all coincide with the principal fiber strains for the cubic fibers. For example, the <111> strain measured for the fibers included not only the axial [111] strains but also the strains in the [11$\bar{1}$], [1$\bar{1}$1], and [$\bar{1}$11] directions which were not in the axial direction of the fibers. In order to compare the measured strains with the computed strains, an averaging of the computed strains was required. This was potentially a difficult problem because of the possible presence of texture in the material. If the spatial distribution and orientations of the fibers were assumed to be completely random (i.e., there was no texture), an average strain could be computed in a simple manner.

Figure 6A:
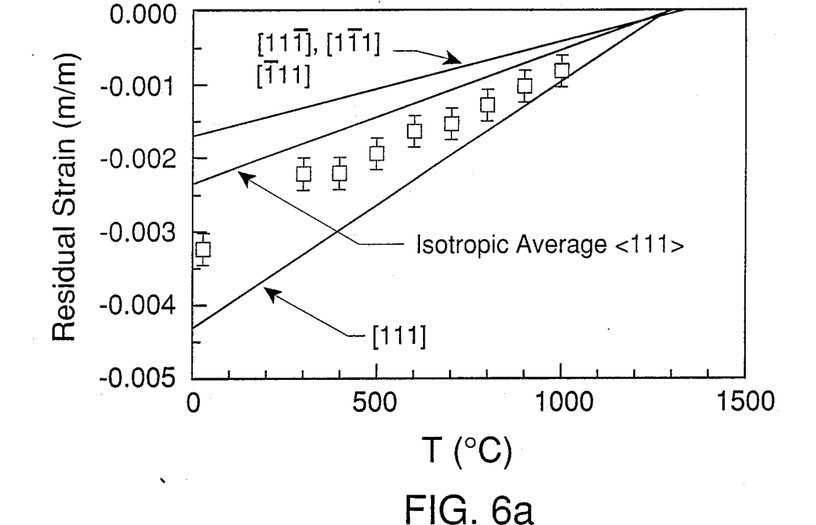
FIGS. 6a, 6b, and 6c are graphs comparing strains in the fiber as predicted by specified models and as measured by the current invention, in the <111> direction (FIG. 6a), in the <220> direction (FIG. 6b), and in the <311> direction (FIG. 6c).
Figure 6B:
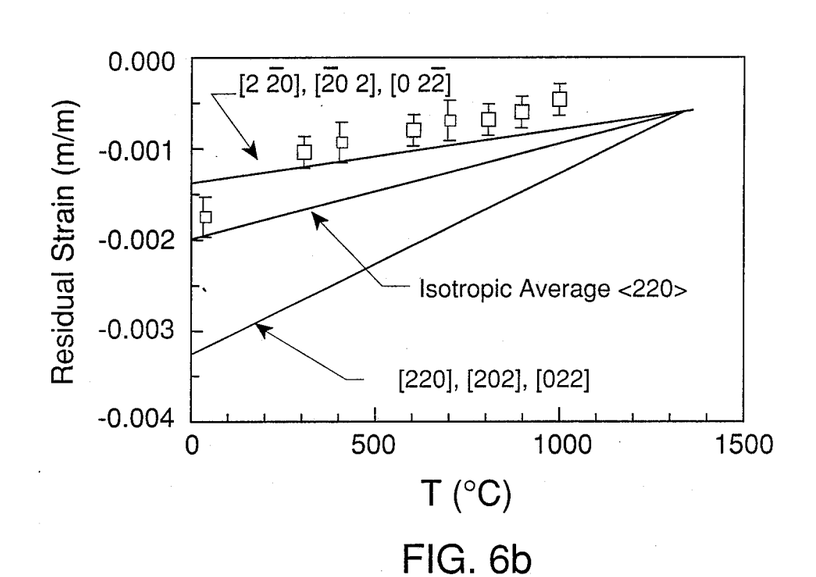
Figure 6C:
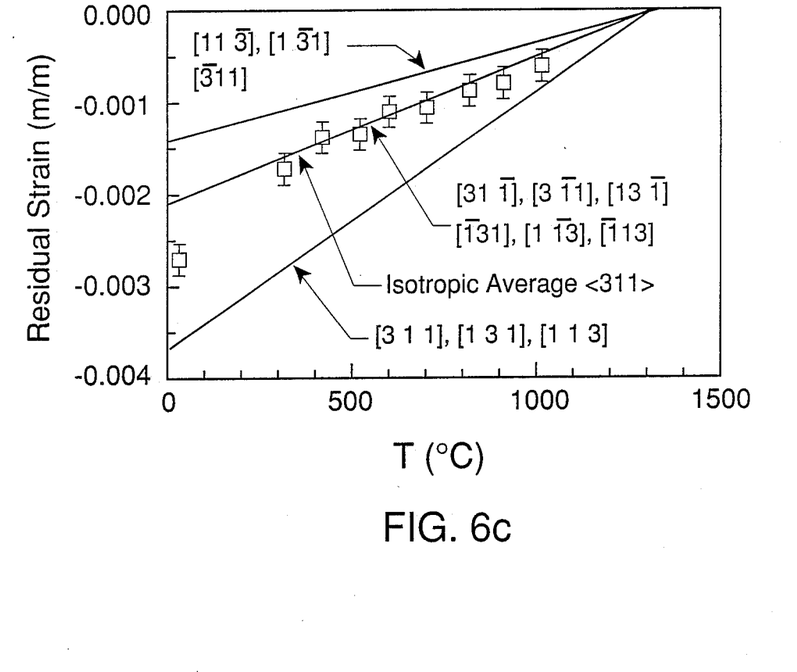

FIGS. 6a, 6b and 6c show comparisons of the measured strains in the <111>, <220> and <311> directions, respectively, of the fibers with computed strains in various individual crystallographic directions as well as their isotropic averages in the same directions, for a composite that has been cooled to various temperatures after firing. In FIG. 6a, the measured <111> strains fell between the computed [111] and the other <111> type strains. In a similar fashion, in FIG. 6b the measured <220> strains fell between the computed <2$\bar{2}$0> type and <220> type strains, and in FIG. 6c the measured <311> strains fell between the computed <311> type, <31$\bar{1}$> type, and <$\bar{3}$11> type strains. Although the predicted isotropic average strains did not agree precisely with the measured strains, they were within 30-40% of the measured values. Considering the fact that the stress models were rather simplified (e.g., interactions between fibers were ignored), these comparisons show good agreements.

As depicted in the preferred embodiment, then, this invention enables the nondestructive, in situ and real time measurement of internal strain between a fiber and a matrix in a stressed sample of a ceramic-matrix or metal-matrix composite, and facilitates the calculation of the resultant stress.

In other embodiments, the method and apparatus of the current invention may be applied as well to determine variations of strain within the volume of a ceramic-matrix or metal-matrix composite by collimating the neutrons, directing them at a specific location within the sample, and examining the diffracted neutrons from the volume interrogated.

As described above, experimental results show that strains measured in ceramic-matrix or metal-matrix composites by the method and apparatus of the current invention are in reasonable agreement with those computed by using various stress models. The current invention may be useful, therefore, for the validation and calibration of other techniques for the measurement of stress (e.g. ultrasonic techniques). It may also be useful for the validation of models used to predict the mechanical behavior of advanced structural composites, including those with complex geometries and the design of models for optimum performance.

The foregoing description of a preferred embodiment of the invention has been presented for purposes of illustration and description. It is not intended to be exhaustive or to limit the invention to the precise form disclosed, and obviously many modifications and variations are possible in light of the above teaching. The embodiments described explain the principles of the invention and practical applications and should enable others skilled in the art to utilize the invention in various embodiments and with various modifications as are suited to the particular use contemplated. It is intended that the scope of the invention be defined by the claims appended hereto.

The embodiments of this invention in which an exclusive property or privilege is claimed are defined as follows:

1. A method for real-time simultaneous measurement of strain in the constituents of a composite comprising:
    directing a polychromatic beam of neutrons from a pulsed source toward a sample,
    orienting a multi-angle diffractometer so that two opposite detectors are on a line perpendicular to said neutron beam,
    measuring, using Bragg's law, the strain on a vector bisecting the angle between said neutron beam and said line perpendicular to said neutron beam.

2. The method of claim 1 wherein said sample is a ceramic-matrix or metal-matrix composite.

3. The method of claim 2 wherein said sample is oriented so that a line parallel to the longitudinal direction of the fiber embedded in said ceramic-matrix or metal-matrix composite bisects the angle between said neutron beam and said line perpendicular to said neutron beam.

4. The method of claim 3 including, calculating, using Bragg's law, the strain parallel to the longitudinal direction of the fibers and the strain perpendicular to the longitudinal direction of the fibers embedded in said ceramic-matrix or metal-matrix composite.

5. The method of claim 4 including collimating said neutron beam and orienting said neutron beam toward a small volume within said ceramic-matrix or metal-matrix composite and measuring the strain within said small volume.

6. The method of claim 5 including orienting said neutron beam toward a multiplicity of small volumes within said ceramic-matrix or metal-matrix composite and averaging the strain measured within said multiplicity of small volumes.

7. The method of claim 4 including calculating the residual stress in a ceramic-matrix or metal-matrix composite by comparing the time-of-flight of neutrons in an unstressed sample to the time of flight of neutrons in a stressed sample.

8. The method of claim 7 including validating models for determination of residual stress by comparing residual stress as projected by said models to the results of said calculations of residual stress.

9. The method of claim 2 wherein said sample is a composite of $Al_2O_3$ and SiC.

10. The method of claim 9 wherein said sample is oriented so that a line parallel to the {111} plane of the SiC whisker bisects the angle between said neutron beam and said line perpendicular to said neutron beam.

11. A method of determining the strain at the fiber-matrix interface in a ceramic-matrix or metal-matrix composite comprising:
   determining the lattice spacing d over a volume of a strain-free powdered sample of a ceramic-matrix or metal-matrix composite,
   determining the lattice spacing $d_0$ associated with a particular lattice plane in a stressed sample of said composite,
   calculating the strain associated with said lattice plane using the formula $e=(d-d_0)/d_0$.

12. An apparatus for the real-time measurement of strain comprising:
   a pulsed neutron source emitting a neutron beam,
   a multi-angle diffractometer oriented so that two opposite detectors are on a line perpendicular to said neutron beam,
   means for determining the time of flight of said diffracted neutrons from a sample to said detectors.

* * * * *